US008852925B2

(12) United States Patent
Halberstadt et al.

(10) Patent No.: US 8,852,925 B2
(45) Date of Patent: Oct. 7, 2014

(54) BIOREACTOR FOR CELL GROWTH AND ASSOCIATED METHODS

(75) Inventors: Craig Halberstadt, Charlotte, NC (US); Richard Peindl, Huntersville, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 2028 days.

(21) Appl. No.: 11/957,747

(22) Filed: Dec. 17, 2007

(65) Prior Publication Data

US 2009/0155908 A1   Jun. 18, 2009

(51) Int. Cl.
| | |
|---|---|
| C12M 1/00 | (2006.01) |
| C12M 3/00 | (2006.01) |
| C12M 1/12 | (2006.01) |
| C12N 5/02 | (2006.01) |
| C12N 5/00 | (2006.01) |
| C12M 1/34 | (2006.01) |

(52) U.S. Cl.
CPC ............. *C12M 25/14* (2013.01); *C12N 5/0068* (2013.01); *C12M 29/04* (2013.01); *C12M 41/00* (2013.01); *C12M 23/34* (2013.01)
USPC .................. 435/294.1; 435/286.5; 435/289.1; 435/297.1; 435/297.2; 435/397

(58) Field of Classification Search
CPC ............................... C12M 25/14; C12M 23/34
USPC .......... 435/294.1, 286.5, 289.1, 297.1, 297.2, 435/397
See application file for complete search history.

(56) References Cited

U.S. PATENT DOCUMENTS

| | | | |
|---|---|---|---|
| 5,081,035 A | | 1/1992 | Halberstadt et al. |
| 5,346,826 A | * | 9/1994 | Andrews ....................... 435/400 |
| 5,605,835 A | | 2/1997 | Hu et al. |
| 5,827,729 A | | 10/1998 | Naughton et al. |
| 5,928,945 A | | 7/1999 | Seliktar et al. |
| 5,932,611 A | * | 8/1999 | Wuthier et al. ............... 514/456 |
| 5,981,211 A | | 11/1999 | Hu et al. |
| 6,008,049 A | | 12/1999 | Naughton et al. |
| 6,218,182 B1 | | 4/2001 | Naughton et al. |

(Continued)

OTHER PUBLICATIONS

Pen-Hsiu Grace Chao, Alan C. West & Clark T. Hung; Article Entitled "Chondrocyte Intracellular Calcium, Cytoskeletal Organization and Gene Expression Responses to Dynamic Osmotic Loading"; *American Journal of Physiology—Cell Physiology*; 39 pages; Aug. 23, 2006.

(Continued)

*Primary Examiner* — Nathan Bowers
*Assistant Examiner* — Gautam Prakash
(74) *Attorney, Agent, or Firm* — Alston & Bird LLP

(57) ABSTRACT

Apparatuses, systems, and methods are provided for growing and maintaining cells. A three-dimensional matrix, such as a hydrogel material, is seeded with cells and placed in a bioreactor having two compartments. The matrix is supported between the two compartments by first and second porous materials, which engage opposing surfaces of the matrix. A first media stream having certain properties is propagated through the first compartment, where it contacts one surface of the matrix via the first porous material. A second media stream having different properties is propagated through the second compartment such that it contacts the opposite surface of the matrix via the second porous material. Through migration of each stream at least partially into the matrix, various controlled gradients may be established within the matrix, encouraging growth of the cells. Such gradients include osmotic pressure, oscillating osmotic pressure, hydrostatic pressure, oxygen tension, and/or nutrient gradients.

13 Claims, 8 Drawing Sheets

(56) References Cited

U.S. PATENT DOCUMENTS

| | | | |
|---|---|---|---|
| 6,387,693 | B2 | 5/2002 | Rieser et al. |
| 6,875,605 | B1 | 4/2005 | Ma |
| 2002/0106625 | A1 | 8/2002 | Hung et al. |
| 2003/0077816 | A1 | 4/2003 | Kronenthal et al. |
| 2005/0002910 | A1 | 1/2005 | Wolfinbarger et al. |
| 2006/0034808 | A1 | 2/2006 | Mizuno |

OTHER PUBLICATIONS

C.R. Halberstadt, B.O. Palsson, A.R. Midgley. & R. L. Curl; Optimization and Mathematical Modeling of the Transtubular Bioreactor for the Production of Monoclonal Antibodies from a Hybridoma Cell Line; *Biotechnology and Bioprocess Engineering*, 7(3); pp. 163-170; 2002.

D.A. Grande, C. Halberstadt, G. Naughton, R. Schwartz & R. Manji; Evaluation of Matrix Scaffolds for Tissue Engineering of Articular Cartilage Grafts; *Journal of Biomedical Materials Research*, 34, #2 pp. 211-220; 1997.

C.R. Halberstadt, R. Hardin, K. Bezverkov, D. Snyder, L. Allen & L. Landeen; The In Vitro Growth of a Three-Dimensional Human Dermal Replacement Using a Single-Pass Perfusion System; *Biotechnology and Bioengineering*; 43; pp. 740-746; 1994.

International Search Report for PCT/US2008/086986; Search completed Mar. 31, 2009.

\* cited by examiner

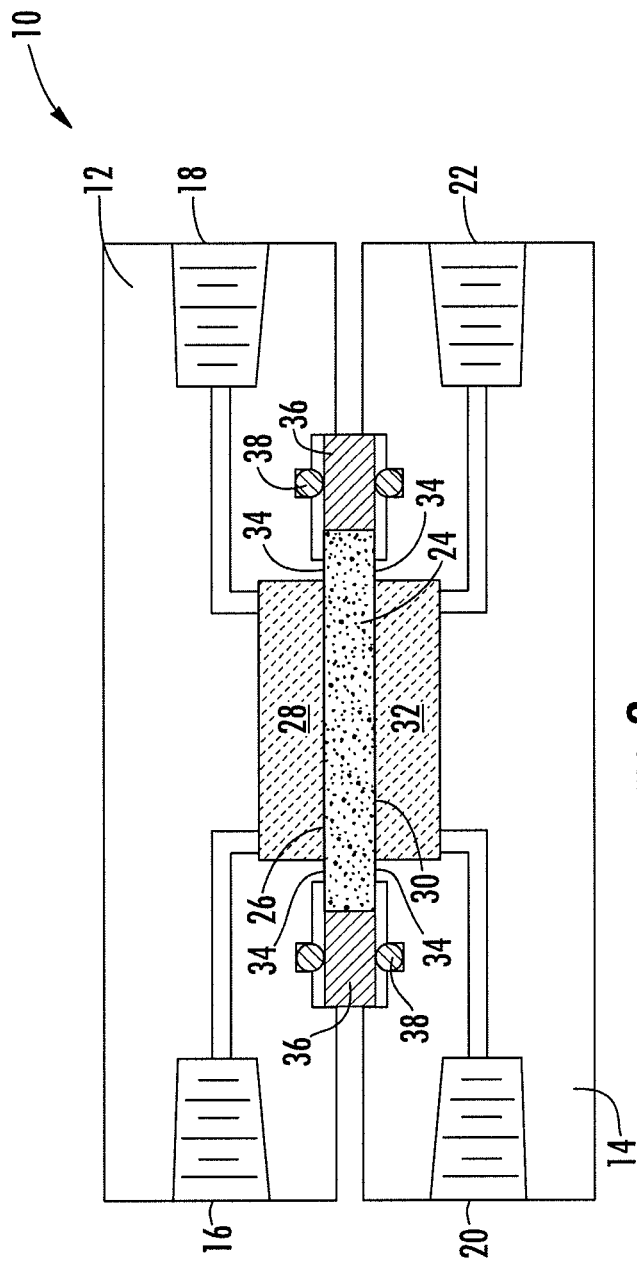
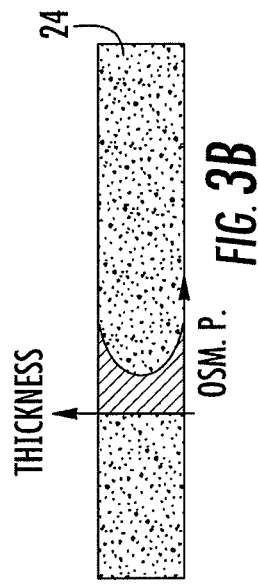
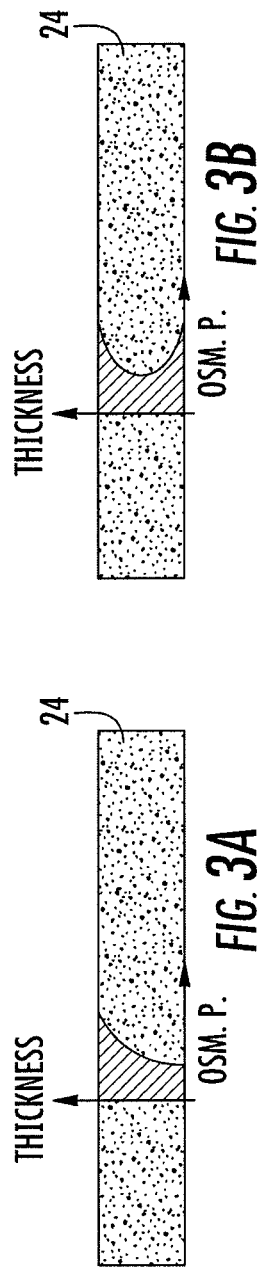

BIOREACTOR FOR CELL GROWTH AND ASSOCIATED METHODS

FIELD OF THE INVENTION

The present invention relates to bioreactors for growing cells and, more particularly, to bioreactors for simulating the effects of mechanical loading and physiologic environmental conditions to facilitate the growth of cells.

BACKGROUND OF THE INVENTION

There is a significant and growing need for the ex vivo creation of mammalian tissues for the augmentation or replacement of damaged tissues and organs. For example, cartilage cells produced in vitro may be useful for repairing cartilage that has been damaged in a knee injury or deteriorated by osteoarthritis.

The successful development of tissues created ex vivo depends on several factors. Such factors may include an adequate cell source that can be grown and differentiated into the desired tissue, a template that will promote cell adhesion and induce the deposition of extracellular matrix proteins, and a growth environment that will foster cell communication.

Different cells must possess different properties for proper functioning in the human body. For example, articular cartilage, or the cartilage that lines bones in joints, is firm and flexible connective tissue that is specialized to absorb and resist compression. Articular cartilage is protected by a nutritive and lubricating medium known as the synovial fluid of the joint. Cartilage is composed of chondrocyte cells, which occupy 10-20% of its volume, and an extracellular material that contains up to 80% water by weight.

The chondrocytes are enclosed within small cavities, called lacunae, generally in groups of 2, 4, or 6 cells as a result of mitosis and restricted cellular movement. The extracellular material consists primarily of large hydrated proteoglycan aggregates entrapped within a matrix of collagen fibrils. The matrix is predominantly made of type II collagen which forms a meshwork of high tensile-strength fibrils. The entrapped proteoglycans (also called mucopolysaccharides) are composed of a core protein that forms a backbone to which many glycosaminoglycan (GAG) chains are covalently attached. The GAGs are high negatively charged molecules that encourage the binding of water and the generation of a large osmotic swelling pressure.

The mechanical behavior of articular cartilage is similar to that of a sponge. During rest, for example when a person is sitting or lying down, the osmotic pressure generated by the proteoglycan aggregates fills the tissue with water up to its maximum capacity. This swelling pressure is contained only by the resilient collagen meshwork. Under load, such as when the person is standing up or walking, the weight of the body compresses the cartilage, squeezing water out until the osmotic pressure generated by the polyglycan produces a swelling force (due to the bound water) equal to the compressive force across the joint. When the load is removed, the cartilage slowly swells back to its full extent.

In order for the tissue created in vitro to function properly, it must have the same properties as the native tissue, or tissue found naturally in the human body. For example, experimental evidence has shown that the application of mechanical stimuli to engineered chondrocytic constructs that emulate the forces applied to articular cartilage leads to the production of a more functional artificially-produced tissue. In other words, tissue developed using the application of mechanical loading is more similar in its content and mechanical properties to physiologic cartilage than tissue produced without mechanical loading.

The main types of mechanical loads that have been investigated include (1) hydrostatic pressure, (2) direct mechanical compression, (3) high and/or low shear forces, (4) forced perfusion, and (5) ultrasonic compression or shear wave induction. Each of these involves the application of actual mechanical stimulation to the cells growing in vitro. A persistent drawback of each of these types of mechanical stimulation, however, is the increased complexity of the system necessary to produce the mechanical load stimulus. This complexity is magnified when production systems are scaled-up for producing large quantities of tissue.

Thus, there is a need for a bioreactor and method for producing and maintaining cells that are similar in content and possess similar mechanical properties to physiologic cells on a large scale with reduced complexity.

BRIEF SUMMARY

The present invention provides systems, apparatuses, and methods for growing cells. In general, a three-dimensional matrix that is seeded with cells is placed in a bioreactor between two compartments. A media stream is propagated through the first compartment, and another media stream having different properties or components is propagated through the second compartment. In this way, each media stream contacts a respective surface of the matrix and migrates at least partially into the matrix, thereby establishing a controlled gradient within the matrix between the two surfaces to encourage the growth of the cells in the matrix. Various types and combinations of gradients may be established, such as an osmotic pressure gradient, an oxygen tension gradient, a nutrient gradient, a hydrostatic pressure gradient, as well as combinations of these gradients. Furthermore, these gradients may be varied as a function of time. For example, the osmolality of one of the streams may be varied as a function of time to create an oscillating osmotic pressure gradient to enhance cell growth and metabolism.

In one embodiment, a system for growing and maintaining cells is provided. The system includes a bioreactor, a source of a first media solution, and a source of a second media solution that is different from the first media solution. The bioreactor has a first compartment having a first inlet, a first outlet in fluid communication with the first inlet, and a first porous material disposed within the first compartment. The bioreactor also has a second compartment adjacent the first compartment that includes a second inlet, a second outlet in fluid communication with the second inlet, and a second porous material disposed within the second compartment. A hydrogel material seeded with cells is disposed between the first compartment and the second compartment and is at least partially supported on a first surface of the hydrogel material by the first porous material and on an opposite, second surface of the hydrogel material by the second porous material. The source of the first media solution is in fluid communication with the first inlet, and the source of the second media solution is in fluid communication with the source of the first media solution and at least one of the first and second inlets. In this way, propagation of at least the first media solution through the first compartment and propagation of the second media solution through the second compartment establishes a controlled gradient across a thickness of the hydrogel material.

Some systems further include a pump in fluid communication with at least one of the sources. The pump is configured to propagate at least one of the media solutions through at least one of the first and second compartments. A controller may also be included, where the controller is configured to control the pump such that a solution comprising at least one of the first and second media solutions is propagated through the first compartment via the first inlet and the second media solution is propagated through the second compartment via the second inlet. In some embodiments, a pinch valve is included between the sources of the first and second media solutions and the first compartment. The pinch valve may be configured to allow a flow of the first media from the respective source to the first inlet and to allow a flow of a solution comprising the first and second media solutions from both the respective sources to the first inlet.

The first media solution may be propagated at a predetermined flow rate that varies as a function of time, and the second media solution may be propagated at a generally constant flow rate such that a hydrostatic pressure gradient that varies as a function of time is established across the thickness of the hydrogel. The first media solution may have a first osmolality and the second media solution may have a second osmolality that is different from the first osmolality such that an osmotic pressure gradient is established across the thickness of the hydrogel. Similarly, the first media solution may have a first oxygen content and the second media solution may have a second oxygen content that is different from the first oxygen content such that an oxygen tension gradient is established across the thickness of the hydrogel. Furthermore, the first media solution may have a first nutrient content and the second media solution may have a second nutrient content that is different from the first nutrient content such that a nutrient gradient is established across the thickness of the hydrogel.

In some cases, the system includes a source of a third media solution having a different osmolality than the first and second media solutions. The first and third media solutions may be alternately propagated through the first compartment to create an oscillating osmotic pressure gradient across the thickness of the hydrogel material. Furthermore, a first sample port may be provided downstream of the first outlet and a second sample port may be provided downstream of the second outlet, such that the sample ports provide access to media exiting the first and second compartments through the first and second outlets, respectively.

In other embodiments, an apparatus for growing and maintaining cells is provided. The apparatus includes a first compartment, a second compartment, and a hydrogel material seeded with cells positioned between the first and second compartments. The first compartment includes a first inlet configured to receive a first media solution, a first outlet in fluid communication with the first inlet, and a first porous material disposed within the first compartment. Similarly, the second compartment includes a second inlet configured to receive a second media solution, a second outlet in fluid communication with the second inlet, and a second porous material disposed within the second compartment. The hydrogel material is at least partially supported on a first surface of the hydrogel material by the first porous material and on an opposite second surface of the hydrogel material by the second porous material. The first media solution is different from the second media solution, and the first and second compartments are configured such that propagation of the first media solution through the first compartment and propagation of the second media solution through the second compartment establishes a controlled gradient across a thickness of the hydrogel material.

The hydrogel material may be seeded with cells that include chondrocytes. Furthermore, the hydrogel material may include sodium alginate, agarose, hyaluronic acid, chondroiton sulfate, collagen, proteoglycan, and/or cell adhesion peptides.

In some cases, the first and second compartments are configured to allow the first media solution to contact the first surface of the hydrogel material and the second media solution to contact the second surface of the hydrogel material. As such, the first media solution and the second media solution may be permitted to contact each other only within the hydrogel material.

In some embodiments, a spacer element is included between the first and second compartments. The spacer element may be configured to partially surround the hydrogel material. The spacer element may also permit sealing of the first surface of the hydrogel material with a portion of the first compartment and sealing of the second surface of the hydrogel material with a portion of the second compartment.

The first compartment may be configured to receive the first media solution having a first osmolality and the second compartment may be configured to receive the second media solution having a second osmolality that is different from the first osmolality such that an osmotic pressure gradient is established across the thickness of the hydrogel. Also, the first compartment may be configured to receive the first media solution having a first oxygen content and the second compartment may be configured to receive the second media solution having a second oxygen content that is different from the first oxygen content such that an oxygen tension gradient is established across the thickness of the hydrogel. Furthermore, the first compartment may be configured to receive the first media solution having a first nutrient content and the second compartment may be configured to receive the second media solution having a second nutrient content that is different from the first nutrient content such that a nutrient gradient is established across the thickness of the hydrogel.

The first compartment may be configured to receive the first media solution at a predetermined flow rate that varies as a function of time, and the second compartment may be configured to receive the second media solution at a generally constant flow rate. Furthermore, the first compartment may be configured to alternately receive the first media solution and a third media solution, where the third media solution has a different osmolality than the first media solution. In this way, alternate propagation of the first and third media solutions through the first compartment may create an oscillating osmotic pressure gradient across the thickness of the hydrogel material. In some cases, each of the first and second inlets and the first and second outlets has an orifice. The orifice of the first inlet may have a larger cross-sectional area than the orifice of the first outlet and the orifice of the second inlet may have approximately the same cross-sectional area as the orifice of the second outlet. In this way, the hydrostatic pressure in the first compartment may be greater than the hydrostatic pressure in the second compartment such that a hydrostatic pressure gradient is created across the thickness of the hydrogel.

In other embodiments, a method of growing cells is provided. A three-dimensional matrix seeded with cells is initially provided, and a first media stream having a first osmolality is propagated across a first surface of the matrix. Likewise, a second media stream having a second osmolality is propagated across a second surface of the matrix that is opposite the first surface. An osmotic pressure gradient is created within the matrix between the first surface and the second surface by migration of the first media stream at least partially into the matrix through the first surface and migration of the second media stream at least partially into the matrix through the second surface, and the creation of the osmotic pressure gradient within the matrix encourages growth of the cells.

In some cases, a hydrogel material is provided that includes sodium alginate, agarose, hyaluronic acid, chondroiton sulfate, collagen, proteoglycan, and/or cell adhesion peptides. Furthermore, the three-dimensional matrix may be seeded with chondrocytes.

The flow rate of the first media stream may be varied as a function of time and the flow rate of the second media solution may be maintained generally constant, thereby varying the hydrostatic pressure gradient across the matrix. In some embodiments, the osmolality of the first media stream may be varied and the osmolality of the second media stream may be maintained generally constant. In this regard, the osmolality of the first media stream may be alternated between an osmolality of approximately 550 mOsm for a predetermined amount of time and approximately 330 mOsm for a predetermined amount of time, and the osmolality of the second media stream may be maintained generally constant at an osmolality of approximately 330 mOsm. The osmolality of the first media stream may be alternated between two different osmolalities once approximately every 3 to 6 hours. In some cases, the osmolality of the first media stream may be alternated between two different osmolalities once approximately every 5 hours.

In some embodiments, a solution that includes basal media, sucrose, and a media including a growth factor, a nutrient, and/or a cytokine may be propagated as the first media stream. Similarly, a solution that includes basal media may be propagated as the second media stream. For example, a solution of at least basal media, sucrose, and TGF-β1 (a growth factor for chondrocytes) may be propagated as the first media stream, and a solution of at least basal media may be propagated as the second media stream. Furthermore, a solution of at least basal media, sucrose, and TGF-β1 and a solution of at least basal media and TGF-β1 may be alternately propagated as the first media stream, and a solution of at least basal media may be propagated as the second media stream.

In other embodiments of a method of growing cells, a hydrogel material seeded with chondrocyte cells may be provided, positioned between a first porous material and a second porous material. A first media stream may be propagated at a predetermined flow rate and a predetermined osmolality through the first porous material, and a second media stream may be propagated at a predetermined flow rate and a predetermined osmolality through the second porous material. The osmolality of the first media stream may be varied and the osmolality of the second media stream may be maintained generally constant to create an oscillating osmotic pressure gradient across the hydrogel material.

In some cases, the osmolality of the first media stream creates an osmotic pressure gradient across the hydrogel material that oscillates between an osmotic pressure gradient of approximately 0 mOsm/mm and approximately 74 mOsm/mm. Furthermore, the osmolality of the first media stream may be alternated between two different osmolalities once approximately every 3 to 6 hours.

In other embodiments of a method of growing cells, a hydrogel material seeded with chondrocyte cells may be provided, positioned between a first porous material and a second porous material. A first media stream having a first oxygen content may be propagated through the first porous material, and a second media stream having a second oxygen content may be propagated through the second porous material. In this way, an oxygen tension gradient may be created within the matrix between a first surface of the hydrogel that is in contact with the first porous material and a second surface of the hydrogel that is in contact with the second porous material by migration of the first media stream at least partially into the matrix through the first surface and migration of the second media stream at least partially into the matrix through the second surface, where creation of the oxygen tension gradient within the matrix encourages the growth of the cells. Thus, oxygen may be removed from the first media stream, and/or nitrogen may be added to the first media stream to displace at least some of the oxygen.

BRIEF DESCRIPTION OF THE SEVERAL VIEWS OF THE DRAWINGS

Figure 1:
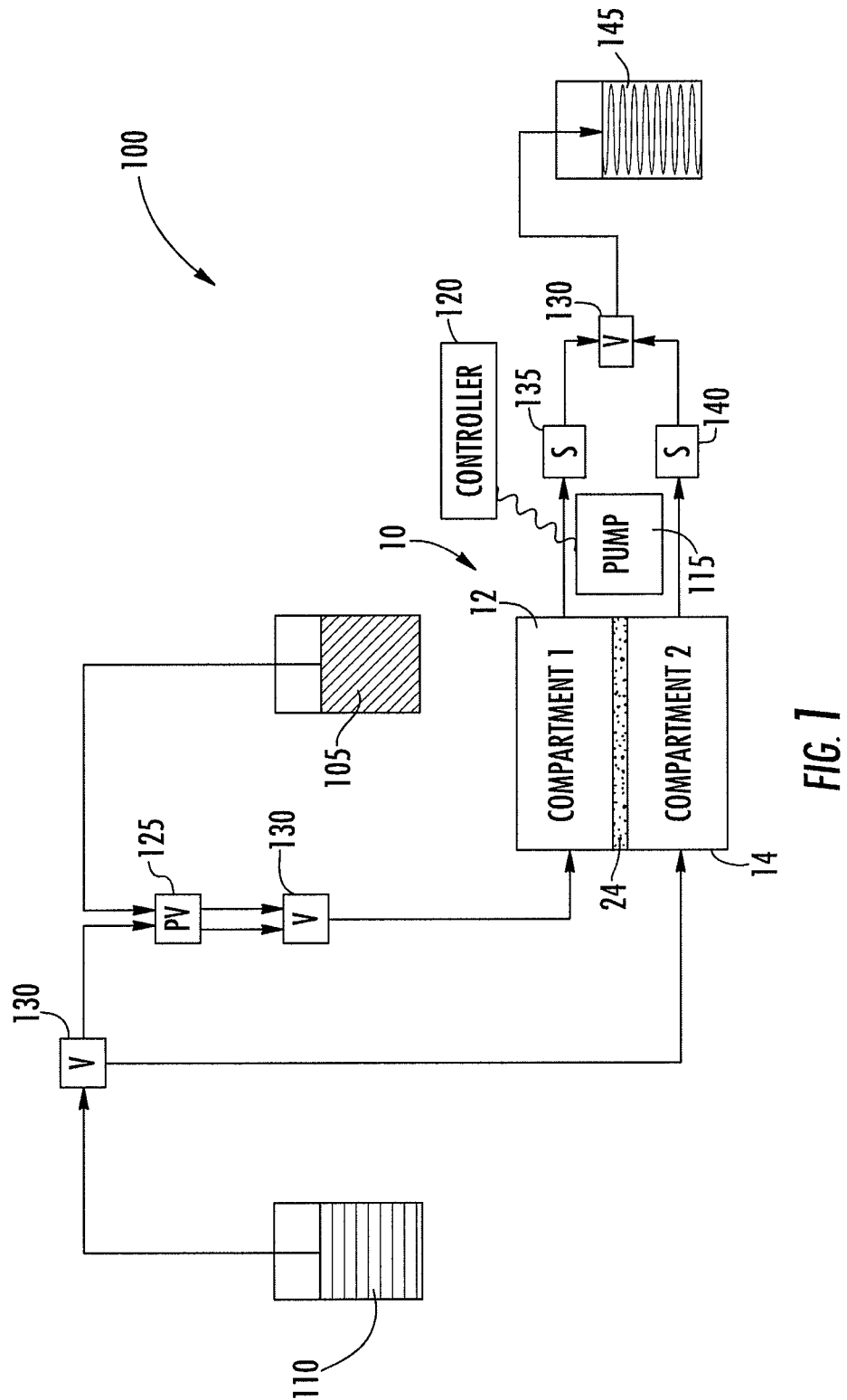
Figure 4:
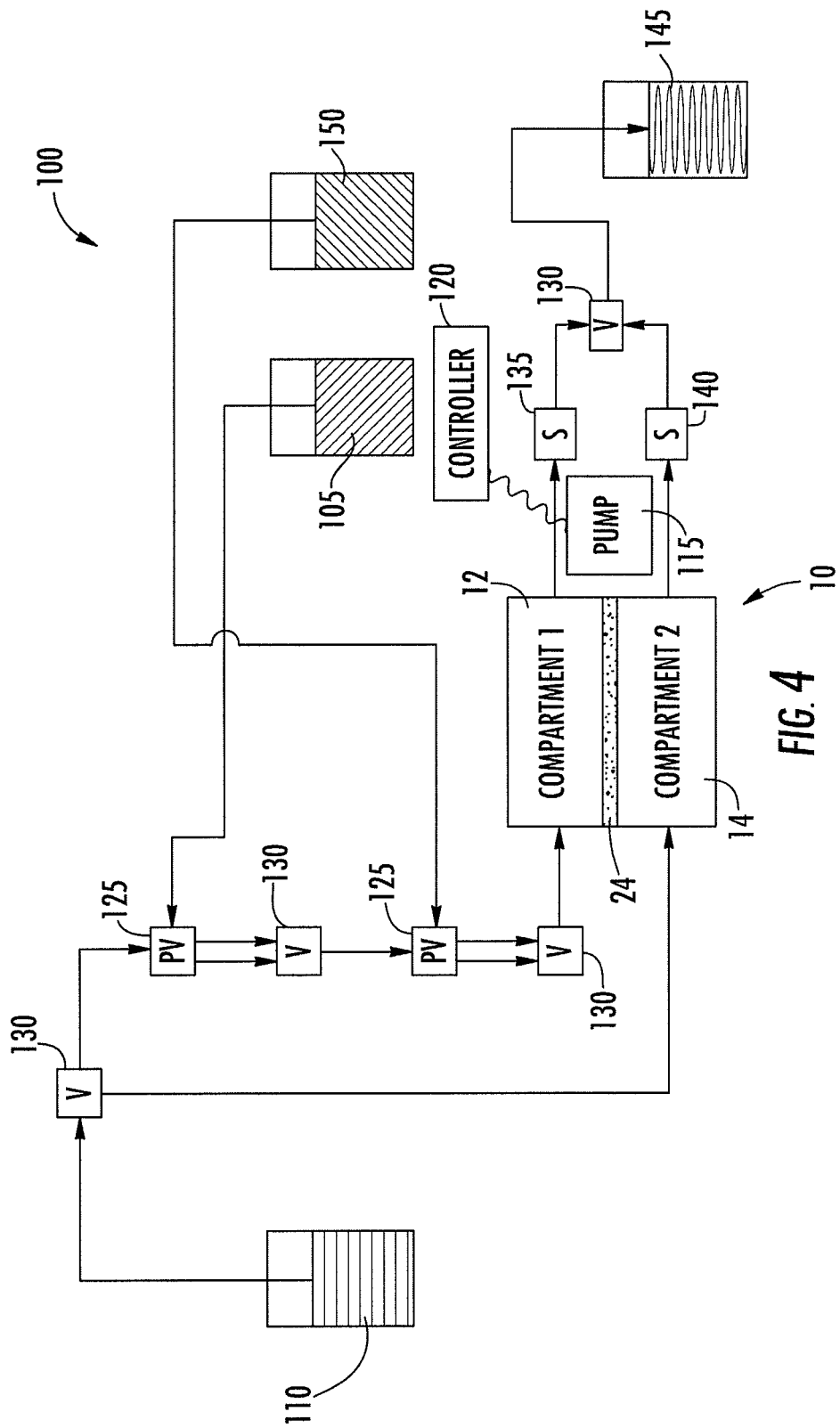
Figure 5:
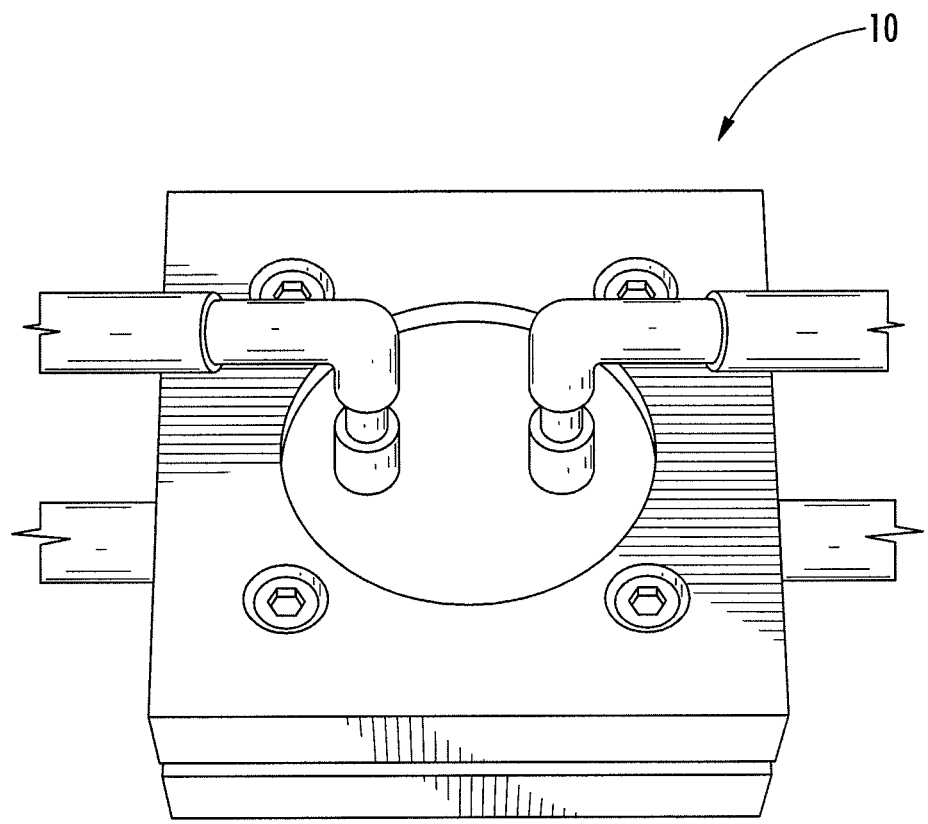
Figure 6:
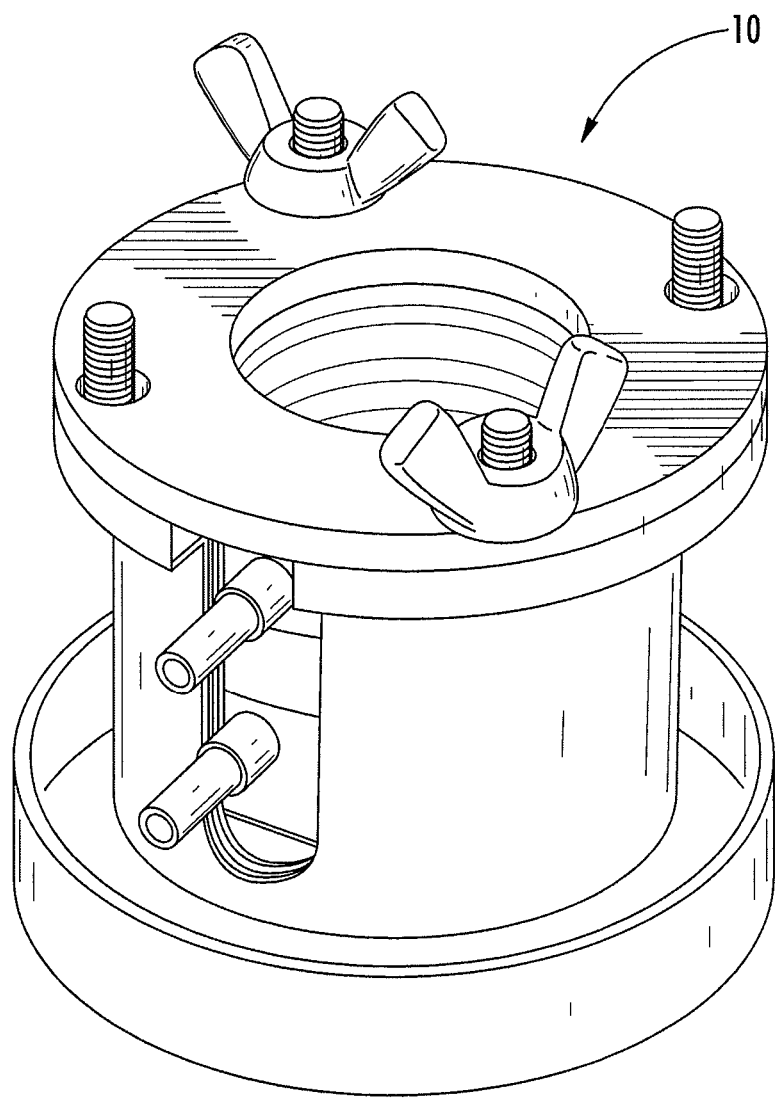
Figure 7:
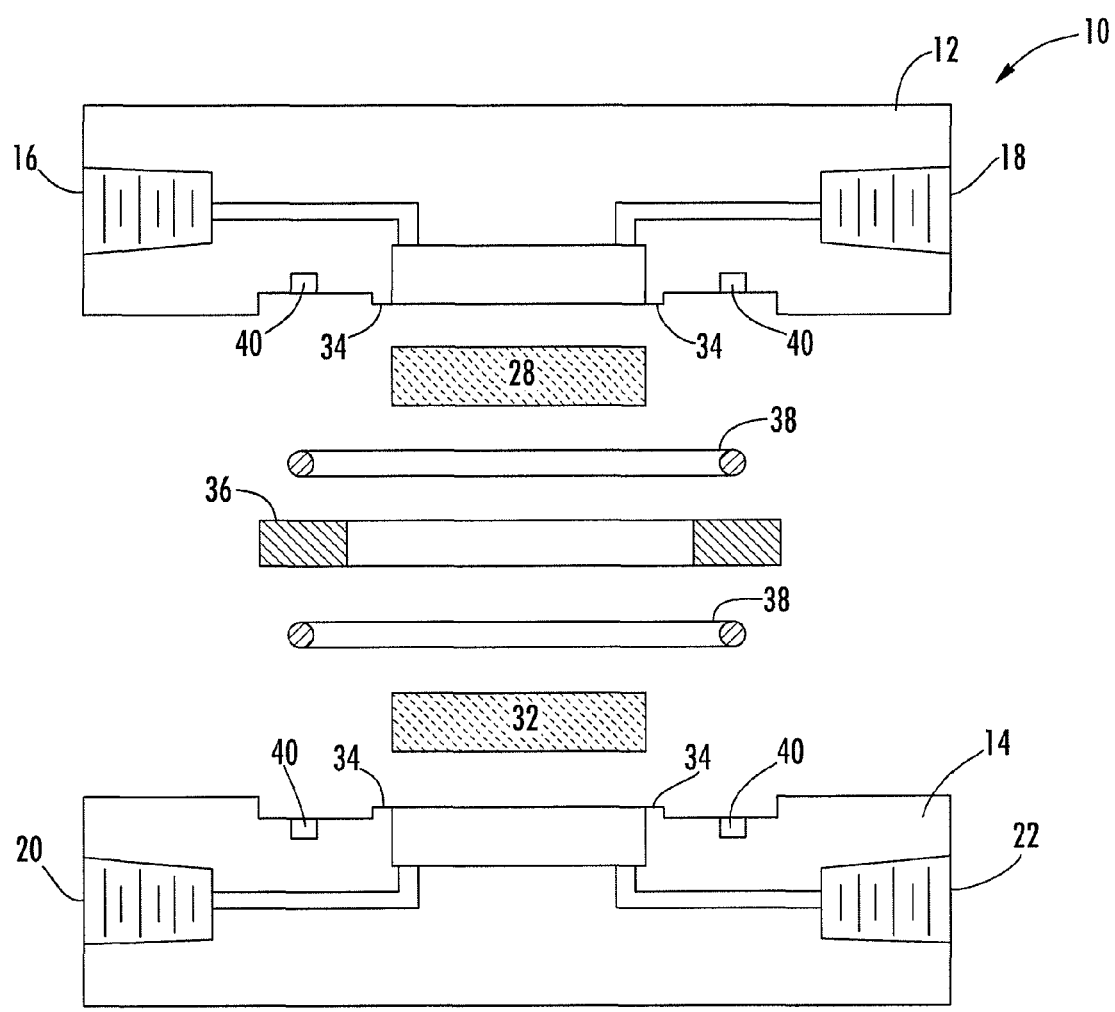
Figure 8G:
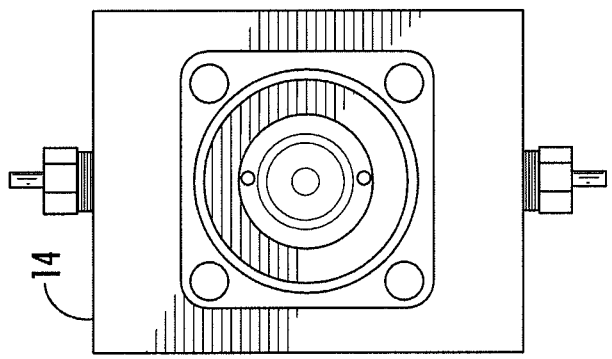
Figures 8D, 8E, 8F:
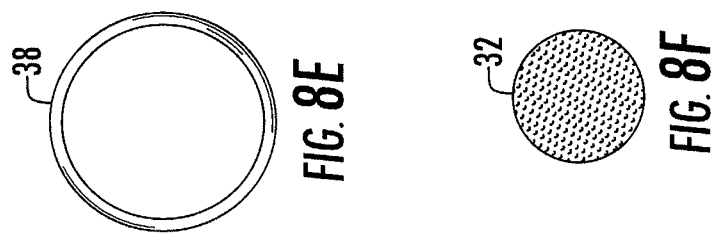
Figures 8B, 8C:
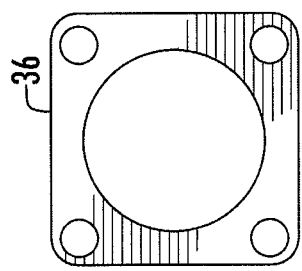
Figure 8A:
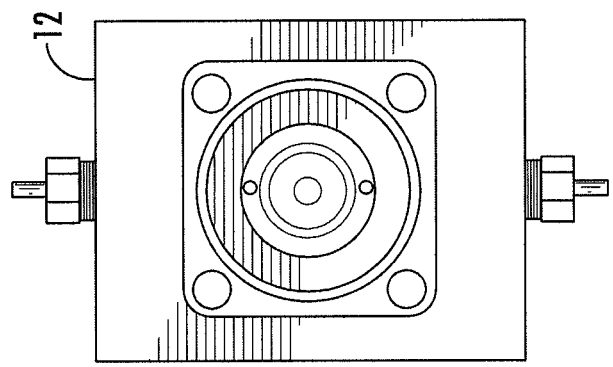
Figure 9:
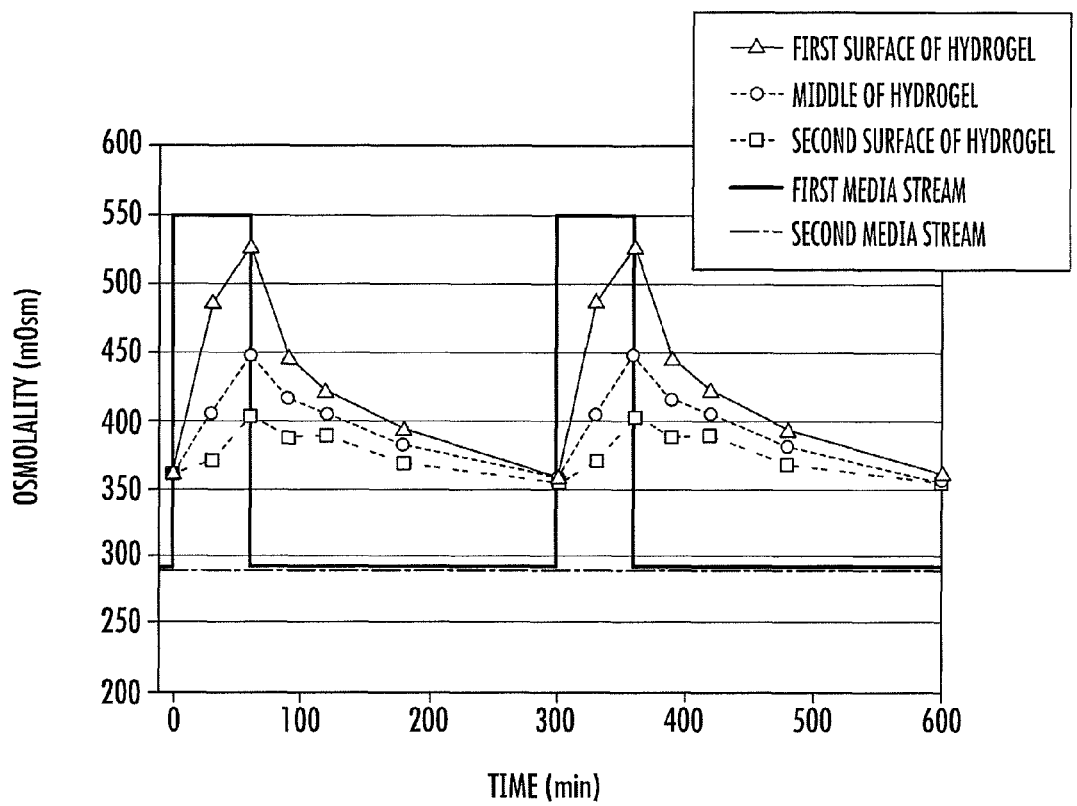
Figure 10:
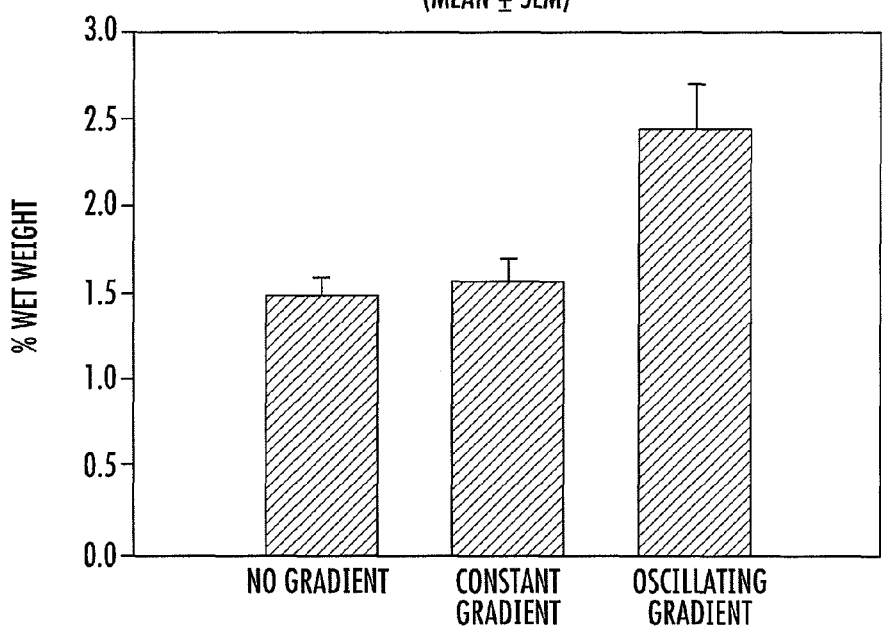

Having thus described the invention in general terms, reference will now be made to the accompanying drawings, which are not necessarily drawn to scale, and wherein:

FIG. 1 is a schematic illustration of a system for growing cells according to one embodiment;

FIG. 2 is a cross-sectional view of a bioreactor according to one embodiment;

FIG. 3A is an illustration of an osmotic pressure gradient across a hydrogel material according to one embodiment, where the osmotic pressure gradient extends from one surface of the hydrogel to the other surface;

FIG. 3B is an illustration of an osmotic pressure gradient that extends from the exterior of the hydrogel towards the center;

FIG. 4 is a schematic illustration of a system for growing cells according to another embodiment;

FIG. 5 is a perspective view of a bioreactor according to one embodiment;

FIG. 6 is a perspective view of a bioreactor according to another embodiment;

FIG. 7 is an exploded cross-sectional side view of the bioreactor of FIG. 2;

FIGS. 8A-8G show the bioreactor of FIG. 2 disassembled;

FIG. 9 depicts temporal media osmolality and the resulting osmolality gradient produced in a hydrogel material under an oscillating osmotic pressure gradient condition; and FIG. 10 depicts sGAG production of cells after 28 days under different bioreactor operating conditions.

DETAILED DESCRIPTION

Embodiments of the present invention now will be described more fully hereinafter with reference to the accompanying drawings, in which some, but not all embodiments of the inventions are shown. Indeed, these embodiments may be in many different forms and should not be construed as limited to the embodiments set forth herein; rather, these embodiments are provided so that this disclosure will satisfy applicable legal requirements. Like numbers refer to like elements throughout.

Bioreactors, systems, and methods are provided for growing and maintaining cells for use in an organism by simulating mechanical loading or existing conditions experienced by the cells in vitro, such as by selectively or preferentially nourishing the separate tissue layers. In general, cells, such as chondrocytes for the building of cartilage, are seeded in a hydrogel material, which is then placed in a bioreactor having two separate compartments. The hydrogel material is supported on one side by a porous material disposed in one of the compartments and on the other side by another porous material disposed in the other compartment. Media solutions are propagated through the two compartments such that each solution contacts the porous material of the respective compartment and, in turn, contacts the surface of the hydrogel supported by the respective porous material. In this way, various types of controlled gradients may be established through the thickness of the hydrogel, allowing different growth factors that promote the growth and metabolism of different cell phenotypes to be delivered to different layers of the hydrogel, promoting the growth of different cell types through the thickness of the hydrogel.

For example, two media solutions having different osmolalities may be propagated through the bioreactor, one through each compartment, to create an osmotic pressure gradient across the hydrogel material. Thus, the osmotic pressure within the hydrogel may be higher at one side of the hydrogel material and may decrease along a thickness of the hydrogel to the other side, simulating in vivo conditions and encouraging the growth of the cells. Furthermore, the osmolality of the media streams may be varied such that the osmotic pressure gradient across the hydrogel oscillates, or cycles between a certain osmotic pressure gradient and no osmotic pressure gradient over a certain period of time, as described below. Oscillation of the osmotic pressure gradient may further encourage growth of cells, such as chondrocytes, which experience similar oscillations in an organism. Other types of gradients, such as an oxygen tension gradient, a nutrient gradient, and/or a hydrostatic gradient, may also be established to facilitate the growth of cells. In this way, tissue constructs in which the physiologic structural architecture and/or cell morphology varies through the thickness of the tissue may be developed.

Systems for Growing Cells

A system 100 for growing and maintaining cells is shown in FIG. 1. The system 100 includes a bioreactor 10, a source of a first media solution 105, as well as a source of a second media solution 110 that is different from the first media solution 105. The bioreactor 10 includes a first compartment 12 and a second compartment 14, and a hydrogel material 24 seeded with cells is positioned between the first and second compartments 12, 14. The bioreactor 10 is configured such that propagation of the first media solution 105 or a mixture of the first and second media solutions 105, 110 through the first compartment 12 of the bioreactor 10 and propagation of the second media solution 110 through the second compartment 14 establishes a controlled gradient across the thickness of the hydrogel material 24, as described below.

Turning to FIG. 2, the first compartment 12 of the bioreactor 10 includes a first inlet 16 and a first outlet 18 in fluid communication with the first inlet 16. Similarly, the second compartment 14 includes a second inlet 20 and a second outlet 22 in fluid communication with the second inlet 20. The hydrogel material 24, which is seeded with cells, is disposed between the first and second compartments 12, 14. In general, cells may be seeded within a hydrogel by mixing the cells in a liquid state and then gelling the material by cooling, heating, or using a chemical reaction. A first surface 26 of the hydrogel 24 is at least partially supported by a first porous material 28, such as a sponge, positioned in the first compartment 12, and an opposite, second surface 30 of the hydrogel 24 is likewise at least partially supported by a second porous material 32 positioned in the second compartment 14.

The compartments 12, 14 are configured such that the first media solution may be propagated into the first compartment 12 through the first inlet 16 and out the first outlet 18. Likewise, the second media solution may be propagated into the second compartment 14 through the second inlet 20 and out the second outlet 22. As media solution flows into each compartment 12, 14, the solution migrates through the respective porous material 28, 32 and contacts the respective surface 26, 30 of the hydrogel 24, at least partially migrating into the hydrogel 24. Thus, propagation of a first media solution having different properties than the second media solution serves to establish a gradient across the thickness of the hydrogel material 24. In this way, the gradient created within the hydrogel material 24 extends from one surface 26, 30 of the hydrogel 24 to the other surface 26, 30, rather than from the exterior of the hydrogel 24 (i.e., multiple surfaces 26, 30) inwards (i.e., towards the center of the hydrogel 24).

For example, an osmotic pressure gradient may be established by using a first media solution having a first osmolality and using a second media solution having a second osmolality that is different from the first osmolality. An illustration of a surface-to-surface osmotic pressure gradient according to embodiments of the present invention is shown in FIG. 3A, while an illustration of a surface-to-center osmotic pressure gradient is shown in FIG. 3B. Likewise, an oxygen tension gradient may be established using media solutions having different oxygen contents; a nutrient gradient may be established using media solutions having different nutrient contents; and a hydrostatic pressure gradient may be established by propagating the first media solution at a flow rate that varies as a function of time and propagating the second media solution at a flow rate that is generally constant, as described below.

Referring again to FIG. 2, the hydrogel material 24 or similar cell-supporting construct may be configured (i.e., sized and shaped) in various ways, depending on the configuration of the bioreactor, the type of cells to be grown, the desired configuration of the end product of the growth, and the particular application of the end product (e.g., in what organism and in what part of the organism the tissue will be used), among other factors. In some embodiments, the size and shape of the hydrogel 24 may be selected to approximate the size and shape of the tissue to be repaired. For example, hydrogel material 24 used for growing cells to be used in articular cartilage repairs in the human body may be in the shape of a disc, have a thickness of about 2-5 mm and have a diameter of about 6-10 mm, reflecting the shape, thickness, and size of the cartilage to be repaired. Thus, an exemplary bioreactor 10 for growing articular cartilage may be configured to receive a hydrogel material 24 formed as a disc with a thickness of approximately 3 mm and a diameter of approximately 15-20 mm. In many cases, a larger graft may be developed, which can then be trimmed to the appropriate size.

The hydrogel material 24 itself may include various chemical compounds and substances to create an appropriate environment and structure for growing and maintaining the desired cells. For example, the hydrogel material may include sodium alginate, agarose, hyaluronic acid, chondroiton sulfate, collagen, and/or proteoglycan, or other hydrogels known to support cellular growth as well as modified hydrogels with cell adhesion peptides or a combination of these hydrogels, among other components. Additionally, the hydrogel 24 may be seeded with various types of cells, including combinations of cells, to grow the desired tissue. For example, the hydrogel may be seeded with chondrocytes to produce cartilaginous tissue, osteoblasts to produce bone, and other types of cells. An example of growing tissue that includes combinations of cells may involve seeding one side of the hydrogel with osteoblasts and seeding the other side of the hydrogel with chondrocytes to produce a cartilage-bone construct.

The porous material 28, 32 that supports the hydrogel 24 may also have various configurations as appropriate considering the configuration of the compartments 12, 14 and the hydrogel 24 to be supported. For a hydrogel disc, for example, each porous material may also be configured as a disc. Generally, the porous material 28, 32 can be sterilizable such that it will not contaminate the hydrogel with which it is in contact and have adequate stiffness to provide support to the central region of the hydrogel 24. For example, in some cases, the porous material 28, 32 may be a sponge, such as that commonly used in wound V.A.C.® applications. In some embodiments, the porous material is macro-porous such that the fluid flow through each compartment is not disrupted.

Turning again to FIG. 1, the media solutions 105, 110 propagated through the bioreactor 10 may include various compounds and nutrients as necessary to provide adequate nutritional support to the growing cells as well as to achieve the desired gradients across the hydrogel material 24. In some embodiments, the first media solution 105 includes growth factors that are known to stimulate growth and/or differentiation of the particular type of cell and components that can alter properties of the solution to achieve the desired type of gradient in a way that is non-toxic to the cells. For example, in systems for growing chondrocytes and where an osmotic pressure gradient across the hydrogel is desired, the first media solution 105 may include Transforming Growth Factor-beta 1 (TGF-β1) or any other growth factor known to promote chondrocyte growth. TGF-β1 is a protein that controls proliferation, differentiation, and other cellular functions. Other growth factors used may include inhibins, activin, anti-müllerian hormone, bone morphogenetic protein, decapentaplegic, and Vg-1, depending on the type of cells to be grown. In this example, the first media solution 105 may also include sucrose or any other compound that can alter the osmolality of the solution, such as sodium chloride, to facilitate the achievement of an osmotic pressure gradient across the hydrogel 24.

The second media solution 110, on the other hand, may be composed of basal media, which may be a solution of components including salts, amino acids, vitamins, and energy sources that establish an appropriate environment for cell life and provide nutrition for cell growth. As an example, basal media used for growing chondrocytes may consist of Dulbecco's Modified Eagle's Medium (DMEM), insulin-transferrin-sodium selenium media supplement (ITS), fetal bovine serum, L-glutamine, L-proline, non-essential amino acids, ascorbic acid, and antibiotic/antimycotic. Continuing the example of establishing an osmotic pressure gradient, the second media solution 110 may have a lower osmolality than the first media solution 105. Thus, by propagating the first media solution 105 (higher osmolality) through the first compartment 12 and propagating the second media solution 110 (lower osmolality) through the second compartment 14, a predetermined osmotic pressure gradient may be established across the hydrogel material 24, as illustrated in FIG. 3A.

The osmotic pressure gradient to be established across the hydrogel material 24 in this case may be determined according to the type of cells to be grown in the hydrogel and the extent of compression/decompression experienced in the native cells in vivo. In other words, the desired osmotic pressure gradient in some embodiments is selected to reflect the forces applied to the cells as they grow naturally within an organism. For example, in some embodiments, the osmolality of the first media solution may be in the range of about 500-600 mOsm, and the osmolality may be adjusted by varying the proportion of sucrose included in the solution. The second media solution may have an osmolality of about 200-400 mOsm. In the case of growing chondrocytes for articular cartilage repairs, the osmolality of the first media solution may be approximately 550 mOsm, and the osmolality of the second media solution may be approximately 330 mOsm. In other embodiments, the osmolalities of the first and second media solutions may be selected such that the osmolality of the first media solution is about 55-75% greater than the osmolality of the second media solution.

Furthermore, a mixture of the first media solution 105 and the second media solution 110 may by propagated through the first compartment 12 in order to decrease the osmolality of the combined solution. In this way, the osmolality of the stream propagated through the first compartment 12 may be varied (for example, as a function of time) by alternately supplying the first media solution 105 alone (higher osmolality) and the combination of the first media solution 105 and the second media solution 110 (lower osmolality). A varying, or oscillating, osmotic pressure gradient may further encourage growth of the cells within the hydrogel by simulating the application and removal of forces upon the cells in vivo. Returning to the example of articular cartilage, cartilage in the human body absorbs water from its surroundings at certain times and expels water at other times, depending on the activity in which the person is engaged. When a person is sitting or lying down, for example, the cartilage in the knees absorbs water (decompression), whereas when the person is standing or walking, the cartilage expels the water (compression). Thus, by varying the osmolality in the first compartment 12 and maintaining the osmolality in the second compartment 14, an oscillating osmotic pressure gradient may be established across the hydrogel material 24 that more closely mimics the conditions experienced by the cells as they grow in an organism. The osmotic pressure gradient may oscillate between a gradient of about 74 mOsm/mm to about 0 mOsm/mm (i.e., no osmotic pressure gradient), depending on the type of cells and the application.

In another example, an oxygen tension gradient may be established across the thickness of the hydrogel. In this case, oxygen may be removed from one of the media solutions, such as the first media solution 105, such that the first media solution 105 has a lesser oxygen content than the second media solution 110 and creates a gradient when the solutions are propagated through the respective compartments 12, 14. Alternatively, oxygen may be displaced from one of the media solutions, such as the first media solution 105, by adding another gas to the solution, such as nitrogen. The oxygen tension gradient may be established across the thickness of the hydrogel by propagating one of the media solutions having an oxygen concentration as high as 21% and the other media solution having an oxygen concentration as low as 0%, depending on the type of cells involved. For example, the first media solution 105 may have an oxygen concentration of 1-5%, and the second media solution 110 may have an oxygen concentration of 17-21%.

An oxygen tension gradient may be established in this way to reflect the depletion of oxygen in the deep layers of certain types of tissue, such as cartilage, due to a relative lack of nutrient, water, and oxygen supply from the much more impermeable bony surface upon which the tissue sits. For example, in the case of cartilage, oxygen (and nutrient) gradients in vivo occur as a result of the surface of the cartilage being exposed to synovial fluid having oxygen and nutrients while the under-surface is attached to relatively impermeable subchondral bone. A nutrient gradient may be established by providing media solutions having different nutrient contents. Thus, for example, the first media solution 105 propagated through the first compartment 12 may have fewer nutrients than the second media solution 110 propagated through the second compartment 14, thereby establishing a nutrient gradient across the thickness of the hydrogel 24.

In addition to or instead of such gradient, a hydrostatic pressure gradient may be established across the hydrogel material 24. For instance, the first media solution 105 may be propagated at a first predetermined flow rate, such as a flow rate of between 0.01 ml/hr. and 10 ml/hr, and the second media solution 110 may be propagated at a second predetermined flow rate that is different from the first flow rate. As an example, the first media solution 105 may be propagated through the first compartment 12 at a flow rate of 5 ml/hr, whereas the second media solution 110 may be propagated through the second compartment 14 at a flow rate of 0.55 ml/hr, thereby establishing a hydrostatic pressure gradient. Furthermore, the flow rate of one of the media solutions may be varied as a function of time to create an oscillating hydrostatic pressure gradient, as described below.

Each of the first and second inlets 16, 20 and the first and second outlets 18, 22 may have an orifice. Thus, in some cases, the hydrostatic pressure gradient may be produced and controlled by varying the inlet and outlet orifice sizes to the compartments 12, 14. For example, by constricting the orifice size of the first outlet 18 of the first compartment 12, such that the orifice of the first inlet 16 has a larger cross-sectional area than the orifice of the first outlet 18, pressure can be built up in the first compartment 12. By creating an elevated pressure in the first compartment 12 and maintaining a lower pressure in the second compartment 14 (by having an equally-sized orifices in second inlet 20 and second outlet 22 of the second compartment 14), a hydrostatic pressure gradient may be created between the first compartment 12 and the second compartment 14 across the thickness of the hydrogel.

The system 100 may include various other components to facilitate the propagation of the first and second media solutions 105, 110 through the compartments 12, 14 of the bioreactor 10. For example, some embodiments may include a pump 115, such as a peristaltic pump, in fluid communication with one or both sources of media solution 105, 110. The pump 115 may be configured to propagate one or both of the media solutions 105, 110 through a respective compartment 12, 14 and may be used in conjunction with a controller 120. The controller 120 (which may, for example, include a computer) may thus be configured to automatically control the pump 115 such that a solution of one or both of the media solutions 105, 110 is propagated through the first compartment 12 via the first inlet (as previously described) and the second media solution 110 is propagated through the second compartment 14 via the second inlet. Furthermore, the controller 120 may be configured to allow a user to set the flow rate of the respective media solution and maintain the desired flow rate generally constant. In FIG. 1, the pump 115 is shown downstream of the bioreactor 10 and is configured to "pull" the media solution(s) through the bioreactor 10; however, the pump 115 may alternatively be located upstream of the bioreactor 10 and configured to "push" the media solution(s) through the bioreactor 10. Furthermore, multiple pumps may be used in the system 100, such as a separate pump for propagating each media solution.

Valves and other flow components may also be included in the system 100. For example, one or more pinch valves 125 may be used at various locations in the system 100, such as shown in FIG. 1, to allow either the first media solution 105 or a mixture of the first media solution 105 and the second media solution 110 to be propagated from the respective sources to the first inlet of the first compartment 12. Other valves 130 may also be used throughout the system 100 to regulate the flow of media solution to the bioreactor 10. The valves 130 may be made of any material suitable for use considering the flow rate and sterile nature of the application, such as stainless steel, and may be any type of valve, such as a ball valve, a gate valve, a pinch valve, a 1-way valve, a 2-way valve, etc., as appropriate.

In some embodiments, one or more sample ports 135, 140 may be included in the system to provide access to media exiting the bioreactor 10. As shown in FIG. 1, a first sample port 135 may be located downstream of the first outlet of the first compartment 12, and a second sample port 140 may be located downstream of the second outlet of the second compartment 14. In this way, the sample ports 135, 140 may be configured to provide access to media exiting the first and second compartments 12, 14 through the first and second outlets, respectively. A user may analyze the media accessed via one or both sample ports 135, 140 to determine whether the bioreactor 10 has been contaminated and/or to evaluate the metabolism of the cells by determining the extent of lactic acid production and glucose consumption, among other uses. In addition, the analysis of media via the sample ports 135, 140 may be performed automatically at predetermined times, such as using a computer-controlled analyzer, and feedback from such analyses may inform the control of other components of the system 100. For example, feedback indicating that glucose consumption has increased may be relayed to one or more of the valves 130, pinch valves 125, pumps 115, or other components, which may also be automatically controlled such that the feedback causes adjustments in the mixture of media solution provided, the flow rates, and/or other variables of the system. Media solution exiting both compartments 12, 14 may then be discarded, such as by being combined into a receptacle of waste solution 145.

Turning to FIG. 4, some embodiments of the system 100 include a source of a third media solution 150 having a different osmolality than the first and second media solutions 105, 110. The first media solution 105 may, for example, include sucrose, whereas the third media solution 150 may not, thereby giving the first media solution 105 a higher osmolality than the third media solution 150. The third media solution 150 may, for example, include TGF-β1 alone, as opposed to TGF-β1 plus sucrose. Thus, the first and third media solutions 105, 150 may be alternately propagated through the first compartment 12 to create an oscillating osmotic pressure gradient across the hydrogel material 24. As shown in FIG. 4, additional valves 130 and pinch valves 125 may be included to allow for alternate propagation of the first and third media solutions 105, 150 through the first compartment 12 and the resulting oscillating osmotic pressure gradient.

Bioreactors for Growing Cells

The bioreactor 10 used in the systems and examples described above may be configured in various shapes and sizes as appropriate for the particular application. For example, FIG. 5 shows a bioreactor 10 having centrally-located inlets 16, 20 and outlets 18, 22, whereas FIG. 2 shows a bioreactor 10 in which the inlets 16, 20 and outlets 18, 22 are located at opposite ends of the first and second compartments 12, 14. In yet another embodiment, the bioreactor 10 may have a cylindrical configuration, as shown in FIG. 6. Furthermore, the volume of the compartments 12, 14 may vary depending on the application. For example, in cases where the osmolality of the media streams is varied to create an oscillating osmotic pressure gradient, as described above, a smaller volume compartment may be desirable to allow the respective compartment to be purged more quickly between solutions.

In any case, referring to FIG. 2, the first and second compartments 12, 14 may be configured to allow the first media solution to contact the first surface 26 of the hydrogel 24 and the second media solution to contact the second surface 30 of the hydrogel 24 in such a way that the first and second media solutions are permitted to contact each other only within the hydrogel material 24. Thus, the first surface 26 may only contact the first media solution, and the second surface 30 may only contact the second media solution, but through migration of the media solutions into the hydrogel material 24, the two solutions may come into contact with each other within the hydrogel 24 itself.

As shown in FIGS. 2 and 7, each compartment 12, 14 may include a ridge 34 configured to engage an edge region of the hydrogel material 24 and to create a seal with the first and second surfaces 26, 30 of the hydrogel 24. The bioreactor 10 may also include various other components to hold the two compartments 12, 14 together and create the appropriate seals to allow propagation of the media solutions into the compartments in the manner described above. For example, in some embodiments, the bioreactor 10 includes a spacer element 36 positioned between the compartments 12, 14, as shown in FIGS. 2 and 7. The spacer element 36 may be configured to partially surround the hydrogel material 24 and to permit sealing of the first surface 26 of the hydrogel material 24 with the ridge 34 of the first compartment 12 and sealing of the second surface 30 of the hydrogel with the ridge 34 of the second compartment 14.

Furthermore, sealing members may be included on either side of the spacer element 36 to provide additional sealing of the bioreactor 10. In the configuration shown in FIGS. 2 and 7, for example, O-rings 38 are used as the sealing members. The O-rings 38 in this example are configured to seat in channels 40 (shown in FIG. 7) formed in the first and second compartments 12, 14. In this way, when the compartments 12, 14 are assembled with the spacer 36 to form the bioreactor 10, the O-rings 38 may engage a corresponding surface of the spacer element 36, thereby reducing the tendency of the ridges 34 to engage the hydrogel 24 with excessive force, which may otherwise damage the hydrogel material, and also providing a secondary seal to prevent the media solutions from leaking out of the bioreactor 10. Thus, the sealing members in some embodiments are compressible sealing members. A top plan view of the disassembled bioreactor 10 of FIGS. 2 and 7, including the first and second compartments 12, 14, spacer element 36, first and second porous materials 28, 32, and O-rings 38, is shown in FIGS. 8A-8G. Other types of sealing members may also be used instead of or in addition to O-rings, such as polymeric foams, adhesives, gels, etc.

Referring again to FIG. 2, in some embodiments, the first compartment 12 may be configured to receive the first media solution at a predetermined flow rate that varies as a function of time, whereas the second compartment 14 may be configured to receive the second media solution at a generally constant flow rate. Depending on the configuration of the bioreactor 10 and the system, media flow rates may range from 0 ml/hr. to 10 ml/hr. For example, the flow rate of the first media solution may alternate between a flow rate of approximately 0.55 ml/hr. for a predetermined time period (such as 5 hours) and 0 ml/hr. for a predetermined time period (such as 5 hours). As the flow rate of the first media solution is alternated, the flow rate of the second media solution may be maintained generally constant, for example at a flow rate of approximately 0.55 ml/hr. In this way, the hydrostatic pressure gradient across the hydrogel material may be varied with time, further encouraging the growth of the cells.

In other embodiments, the first compartment 12 may be configured to alternately receive the first media solution and a third media solution, for example when used in a system similar to the system depicted in FIG. 4. In this case, the third media solution has an osmolality that is different from the first media solution such that alternate propagation of the first and third media solutions through the first compartment 12 and propagation of the second media solution through the second compartment 14 creates an oscillating osmotic pressure gradient across the hydrogel material, as previously discussed. In some embodiments, the first media solution may have an osmolality that is about 55-75% greater than the osmolality of the second media solution, whereas the third media solution may have the same osmolality as the second media solution. In this way, the osmotic pressure gradient may vary between a predetermined gradient, such as 74 mOsm/mm and relatively no gradient at all. For example, the first media solution may have an osmolality of approximately 550 mOsm, the second media solution may have an osmolality of approximately 330 mOsm, and the third media solution may have an osmolality of approximately 330 mOsm. The first and third media solutions may be alternately propagated through the first compartment 12, each for a predetermined amount of time (varying the osmolality between 550 mOsm and 330 mOsm), while the second media solution is propagated through the second compartment (maintaining the osmolality at 330 mOsm).

The first and third media solutions may be cycled (i.e., alternated) once approximately every 3 to 6 hours. For example, in an application to grow chondrocyte cells for an articular cartilage repair of a human being, the first and third media solutions may be cycled through the first compartment 12 once approximately every 5 hours to simulate the compression and decompression experienced by cartilage within the human body. In other words, cartilage in the human body absorbs water from its surroundings at certain times and expels water at other times, like a sponge, depending on the activity in which the person is engaged. When a person is sitting or lying down, for example, the cartilage in the knees absorbs water, whereas when the person is standing or walking, the cartilage expels the water. Thus, a cycle time of 5 hours may be chosen to simulate the compression/decompression that may occur in knee cartilage when a person sits for 5 hours and stands for 5 hours.

Methods of Growing Cells

In other embodiments, a method of growing cells is provided. A three-dimensional matrix is initially seeded with cells, such as chondrocytes, as previously described. A first media stream having a first osmolality is then propagated across a first surface of the matrix, and a second media stream having a second osmolality is propagated across a second surface of the matrix that is opposite the first surface. An osmotic pressure gradient may thus be created by the migration of the first media stream at least partially into the matrix through the first surface and migration of the second media stream at least partially into the matrix through the second surface. In this way, the creation of the osmotic pressure gradient within the matrix, such as that depicted in FIG. 3A, encourages growth of the cells.

As previously described, the three-dimensional matrix may be a hydrogel material that includes one or more chemical compounds and substances, such as sodium alginate, agarose, hyaluronic acid, chondroiton sulfate, collagen, and/or proteoglycan, among others. The components of the hydrogel may be selected based on various factors, such as the type of cells to be grown and the particular application.

In some cases, the flow rate of the first media stream may be varied as a function of time while the second media stream may be maintained at a generally constant flow rate. As previously mentioned, in an exemplary embodiment, the flow rate of the first media stream may be alternated between a higher flow rate and a lower flow rate. For example, the first media stream may be propagated at a flow rate of approximately 0.55 ml/hr. for a predetermined time period (such as 5 hours) and 0 ml/hr. for a predetermined time period (such as 5 hours). The flow rate of the second media stream, however, may be maintained generally constant, for example at a flow rate of approximately 0.55 ml/hr. In this way, the hydrostatic pressure gradient across the seeded matrix may be varied with time, encouraging the growth of the cells.

Embodiments of the method of growing cells may also include varying the osmolality of the first media stream and maintaining the second media stream at a generally constant osmolality. As described above, the osmolality of the first media stream may be alternated between a higher osmolality of 500-600 mOsm (e.g., an osmolality of approximately 550 mOsm) for a predetermined amount of time and a lower osmolality of about 250-400 mOsm (e.g., an osmolality of approximately 330 mOsm) for a predetermined amount of time. For example, the osmolality may be alternated by combining different media solutions having different osmolalities. The second media stream may be maintained at a generally constant osmolality, such as a lower osmolality of approximately 330 mOsm. Furthermore, the osmolality of the first media stream may be alternated between two different osmolalities once approximately every 3 to 6 hours. In the case of growing chondrocytes, for example, the osmolality may be alternated approximately every 5 hours.

As described above, the first media solution may include growth factors that are known to stimulate growth and/or differentiation of the particular type of cell and components that can alter properties of the solution to achieve the desired type of gradient in a way that is non-toxic to the cells, such as growth factors that include inhibins, activin, anti-müllerian hormone, bone morphogenetic protein, decapentaplegic, and Vg-1, depending on the type of cells to be grown. The first media solution may also include sucrose or any other compound that can alter the osmolality of the solution, such as sodium chloride, to facilitate the achievement of an osmotic pressure gradient across the hydrogel. In addition, the first media solution may include a growth factor, a nutrient, and/or a cytokine. For example, the first media stream may include basal media plus TGF-β1 plus sucrose, whereas the second media stream may include only basal media. In another example, a solution of basal media plus TGF-β1 plus sucrose may be propagated alternately with a solution of basal media plus TGF-β1 as the first media stream through the first compartment, and the second media stream of basal media solution only may be propagated through the second compartment to provide an oscillating osmotic pressure gradient.

In other embodiments, a method of growing cells may be provided that includes providing a hydrogel material seeded with chondrocyte cells disposed between a first porous material and a second porous material. A first media stream may be propagated at a predetermined flow rate and a predetermined osmolality through the first porous material, and a second media stream may be propagated at a predetermined flow rate and a predetermined osmolality through the second porous material. The osmolality of the first media stream may be varied while the osmolality of the second media stream is maintained generally constant to create an oscillating osmotic pressure gradient across the hydrogel material, as described above.

For example, the osmolality of the first media stream may be varied such that the osmotic pressure gradient across the hydrogel material oscillates between an osmotic pressure gradient of approximately 0 mOsm/mm and approximately 74 mOsm/mm. Furthermore, the osmolality of the first media stream may be alternated between two different osmolalities once approximately every 3 to 6 hours.

In yet another embodiment, a hydrogel material seeded with cells and disposed between a first porous material and a second porous material may be provided. A first media stream having a first oxygen content may be propagated through the first porous material, and a second media stream having a second oxygen content may be propagated through the second porous material. In this way, an oxygen tension gradient may be created within the matrix between a first surface of the hydrogel that is in contact with the first porous material and a second surface of the hydrogel that is in contact with the second porous material by migration of the first media stream at least partially in the matrix through the first surface and migration of the second media stream at least partially into the matrix through the second surface. The creation of the oxygen tension gradient within the matrix serves to encourage the growth of the cells, as previously discussed.

In some cases, oxygen is removed from one of the media streams to create the oxygen tension gradient. For example, oxygen may be removed from the second media stream such that the second media stream has a lesser oxygen content than the first media stream. In other cases, a gas, such as nitrogen, may be added to one of the media streams to displace at least some of the oxygen. For example, nitrogen may be added to the second media stream to displace some of the oxygen such that the second media stream has a lesser oxygen content than the first media stream.

An Example—The Effect of Ultra-Low Frequency Osmotic Oscillations on Chondrocytes In an experiment conducted to examine the effect of ultra-low frequency osmotic oscillations on chondrocyte viability and matrix production, for example, chondrocytes were seeded in a hydrogel material and cultured under three different conditions: (1) no osmotic pressure gradient; (2) a static osmotic pressure gradient; and (3) an oscillating osmotic pressure gradient. Cartilage was harvested from freshly euthanized juvenile pigs according to a protocol approved by the Institutional Animal Care and Use Committee (IACUC). Chondrocytes were then isolated from the cartilage stepwise using hyaluronidase, protease, and collaginase. The isolated chondrocytes were seeded at 110,000 cells/cm$^2$ in monolayer and grown to confluence in media consisting of DMEM, 10% fetal bovine serum, and 1% antibiotic/antimycotic at a temperature of 37° C. and 5% $CO_2$. The cells were then released and seeded into hydrogel discs. The hydrogel discs had a 2% agarose content, were 27 mm in diameter, and had a thickness of 3 mm at a final density of 20 million cells/ml. The discs were then placed in bioreactors similar to the bioreactor 10 shown in FIG. 2 and operated under the three conditions mentioned above.

Three media solutions were used in a system similar to the system 100 shown in FIG. 4 to achieve the three operating conditions. The three media solutions consisted of: (1) basal media (osmolality of approximately 330 mOsm); (2) basal media plus TGF-β1 (osmolality of approximately 330 mOsm); and (3) basal media plus TGF-β1 plus sucrose (osmolality of approximately 550 mOsm). The basal media solution consisted of DMEM, ITS (5 mcg/5 mcg/5 ng/ml), fetal bovine serum 2%, L-glutamine 2 mM, L-proline 50 mcg/ml, non-essential amino acids 0.1 mM, ascorbic acid 50 mcg/ml, and antibiotic/antimycotic 1%. The TGF-β1 was combined with the basal media and with the basal media plus sucrose solutions at 1 ng/ml. The media solutions were propagated through the bioreactor compartments at a flow rate of approximately 0.55 ml/hr, and the bioreactors were operated for 28 days at 37° C. and 5% $CO_2$.

The condition of no osmotic pressure gradient was achieved by propagating basal media plus TGF-β1 through the first compartment of the bioreactor and propagating only basal media through the second compartment, such that the osmolality of the solution in both compartments was 330 mOsm. A static osmotic pressure gradient was achieved by propagating basal media plus TGF-β1 plus sucrose through the first compartment and propagating only basal media through the second compartment, such that the first compartment experienced a constant osmolality of about 550 mOsm and the second compartment experienced a constant osmolality of 330 mOsm. An oscillating osmotic pressure gradient was achieved by alternately propagating basal media plus TGF-β1 plus sucrose and basal media plus TGF-β1 (no sucrose) through the first compartment and propagating only basal media through the second compartment. Thus, under the third operating condition, the osmolality of the first compartment alternated between 550 mOsm and 330 mOsm, while the osmolality of the second compartment was maintained at 330 mOsm. The temporal media osmolality and resulting osmolality gradient produced in the hydrogel material for the condition of an oscillating osmotic pressure gradient, where the osmolality of the first compartment was changed every 5 hours, is shown in FIG. 9.

After 28 days, the hydrogel material was removed from each bioreactor and analyzed to evaluate the growth of the cells. Following papain digestion, sulfated glycosaminoglycan (sGAG) content was determined by dimethyl-methylene blue (DMMB) assay, collagen content was determined by hydroxyproline assay, and DNA content was determined by pico-green/calf thymus assay. The sGAG results were qualitatively verified using Toludine Blue staining of formalin/ethanol fixed, paraffin processed specimens. sGAGs are long polysaccharide molecules that are a major structural component of cartilage. These molecules help bind water in the cartilage extracellular matrix.

It was found that exposure to higher osmolality environments resulted in improvements in sGAG content, both under steady state and oscillating osmotic pressure gradient conditions. The content of sGAG in the operating condition involving no osmotic pressure gradient was 1.49% wet weight. In the steady state and oscillating osmotic pressure gradient conditions, sGAG content improved to 1.61% wet weight and 2.45% wet weight, respectively. Thus, applying a steady state osmotic pressure gradient across the hydrogel improved sGAG content by 7.8% over having no osmotic pressure gradient, and applying an oscillating osmotic pressure gradient improved sGAG content by 64% over the no gradient condition. FIG. 10 shows the wet weight percentage of sGAG for each of the three conditions. Only trace amounts of collagen (<0.15%) were created under any of the three conditions, which may indicate that the process had not gone on long enough or that the cycling load may not have been optimized, among other reasons. Furthermore, chondrocyte metabolism (glucose consumption vs. lactate production) was enhanced under conditions involving a static or oscillating osmotic pressure gradient. These results indicate that growth of cells, such as chondrocytes, is encouraged when an osmotic pressure gradient is achieved across the three-dimensional matrix, and even more so when an oscillating osmotic pressure gradient is achieved.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of growing cells comprising:
   providing a hydrogel material seeded with chondrocyte cells disposed between a first porous material and a second porous material;
   propagating a first media stream at a predetermined flow rate and a predetermined osmolality through the first porous material;
   propagating a second media stream at a predetermined flow rate and a predetermined osmolality through the second porous material; and
   varying the osmolality of the first media stream and maintaining the osmolality of the second media stream generally constant to create an oscillating osmotic pressure gradient across the hydrogel material.

2. The method of claim 1, wherein varying the osmolality of the first media stream creates an osmotic pressure gradient across the hydrogel material that oscillates between an osmotic pressure gradient of approximately 0 mOsm/mm and approximately 74 mOsm/mm.

3. The method of claim 1, wherein varying the osmolality of the first media stream comprises alternating between two different osmolalities once approximately every 3 to 6 hours.

4. The method of claim 1, wherein varying the osmolality of the first media stream comprises alternating between an osmolality of approximately 550 mOsm for a predetermined amount of time and approximately 330 mOsm for a predetermined amount of time, and wherein maintaining a generally constant osmolality of the second media stream comprises maintaining a generally constant osmolality of approximately 330 mOsm.

5. A method of growing cells comprising:
   providing a three-dimensional matrix seeded with cells;
   propagating a first media solution having a first osmolality across a first surface of the matrix;
   propagating a second media solution having a second osmolality across a second surface of the matrix that is opposite the first surface; and
   propagating a third media solution across the first surface of the matrix alternately with the first media solution, wherein the third media solution has a third osmolality that is different from the first osmolality, and wherein the alternate propagation of the first and third media solutions creates an oscillating osmotic pressure gradient within the matrix between the first surface and the second surface by migration of the first and third media solutions at least partially into the matrix through the first surface and migration of the second media solution at least partially into the matrix through the second surface;
   wherein the creation of the oscillating osmotic pressure gradient within the matrix encourages growth of the cells.

6. The method of claim 5, wherein providing the three-dimensional matrix comprises providing a hydrogel material that includes at least one substance selected from the group consisting of sodium alginate, agarose, hyaluronic acid, chondroiton sulfate, collagen, proteoglycan, and cell adhesion peptides.

7. The method of claim 5, wherein providing the three-dimensional matrix comprises seeding the three-dimensional matrix with chondrocytes.

8. The method of claim 5 further comprising varying the flow rate of at least one of the first media solution or the third media solution as a function of time, wherein propagating the second media solution comprises maintaining a generally constant flow rate of the second media solution, thereby varying the hydrostatic pressure gradient across the matrix.

9. The method of claim 5, wherein the first and third media solutions are alternated once approximately every 3 to 6 hours.

10. The method of claim 5, wherein the first and third media solutions are alternated once approximately every 5 hours.

11. The method of claim 5, wherein propagating the first media solution comprises propagating a solution comprising basal media, sucrose, and a media including at least one compound selected from the group consisting of a growth factor, a nutrient, and a cytokine, and wherein propagating the second media solution comprises propagating a solution comprising basal media.

12. The method of claim 5, wherein propagating the first media solution comprises propagating a solution comprising basal media, sucrose, and TGF-$\beta$1, and wherein propagating the second media solution comprises propagating a solution comprising basal media.

13. The method of claim 5, wherein propagating the third media solution comprises propagating a solution comprising basal media and TGF-$\beta$1.

* * * * *